United States Patent [19]

Joshua et al.

[11] Patent Number: 4,968,693
[45] Date of Patent: Nov. 6, 1990

[54] 3-KETO HMG-COA REDUCTASE INHIBITORS

[75] Inventors: Henry Joshua, Staten Island, N.Y.; Kenneth E. Wilson, Westfield, N.J.; Michael S. Schwartz, Glenside, Pa.; Ta J. Lee, Lansdale, Pa.; Gerald E. Stokker, Gwynedd Valley, Pa.

[73] Assignee: Merck & Co., Inc., Rahway, N.J.

[21] Appl. No.: 363,792

[22] Filed: Jun. 9, 1989

Related U.S. Application Data

[63] Continuation-in-part of Ser. No. 162,785, Mar. 2, 1988, abandoned.

[51] Int. Cl.$^5$ .................... A61K 31/36; C02D 309/30
[52] U.S. Cl. .................... 514/460; 514/459; 514/824; 549/292
[58] Field of Search ................ 549/292; 514/159, 460, 514/824

[56] References Cited

U.S. PATENT DOCUMENTS

| | | | |
|---|---|---|---|
| 4,361,515 | 11/1982 | Terahara et al. | 549/292 |
| 4,517,373 | 5/1985 | Terahara et al. | 549/292 |
| 4,582,915 | 4/1986 | Sleteinger et al. | 549/292 |
| 4,833,258 | 5/1989 | Smith et al. | 549/292 |
| 4,857,522 | 8/1989 | Di Pietro et al. | 514/459 |

FOREIGN PATENT DOCUMENTS 59-186972  10/1984  Japan .................... 549/292

*Primary Examiner*—Richard L. Raymond
*Assistant Examiner*—Mark W. Russell
*Attorney, Agent, or Firm*—Melvin Winokur; Joseph F. DiPrima

[57] ABSTRACT

Compounds of formula (I) and (II):

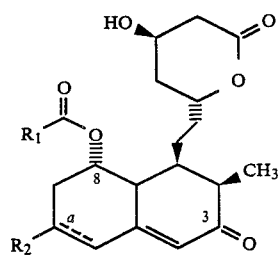

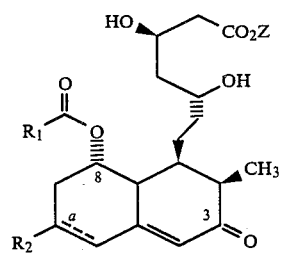

are HMG-CoA reductase inhibitors.

10 Claims, No Drawings

3-KETO HMG-COA REDUCTASE INHIBITORS

This application is a continuation-in-part of Ser. No. 162,785 now abandoned filed Mar. 2, 1988.

BACKGROUND OF THE INVENTION

Hypercholesterolemia is known to be one of the prime risk factors for ischemic cardiovascular disease, such as arteriosclerosis. Bile acid sequestrants have been used to treat this condition; they seem to be moderately effective but they must be consumed in large quantities, i.e. several grams at a time and they are not very palatable.

MEVACOR TM (lovastatin), now commercially available, is one of a group of very active antihypercholesterolemic agents that function by limiting cholesterol biosynthesis by inhibiting the enzyme, HMG CoA reductase. In addition to the natural fermentation products, mevastatin and lovastatin, there are a variety of analogs thereof, produced by microbial, enzymatic and synthetic techniques.

The naturally occurring compounds and their analogs have the following general structural formulae:

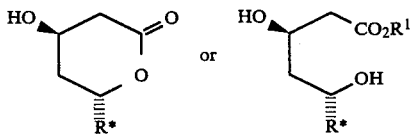

wherein:

$R^1$ is hydrogen, $C_{1-5}$ alkyl or $C_{1-5}$ alkyl substituted with a member of the group consisting of phenyl, dimethylamino, or acetylamino; and R* is

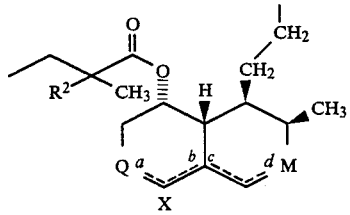

wherein
Q is

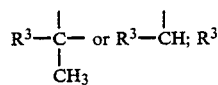

is H or OH or Q is

M is

$R^4$ is hydrogen or hydroxy; X is $CR^5R^6$, O, S, or NH; $R^5$ and $R^6$ are H, OH, or $OR^7$ where $R^7$ represents a phosphoryl or acyl moiety;

$R^2$ is hydrogen or methyl; and a, b c, and d represent single bonds, one of a, b, c or d represents a double bond, or both a and c or both b and d represent double bonds provided that when a is a double bond, Q is

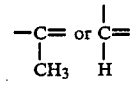

and when d is a double bond, M is

and provided that when $R^5$ or $R^6$ is OH or $OR^7$ or X is O, S, or NH, a, b, and c are single bonds U.S. Pat. No. 4,517,373 discloses hydroxy containing compounds represented by the above general formula wherein R* is

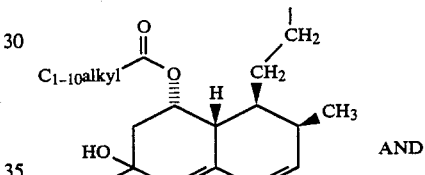

AND

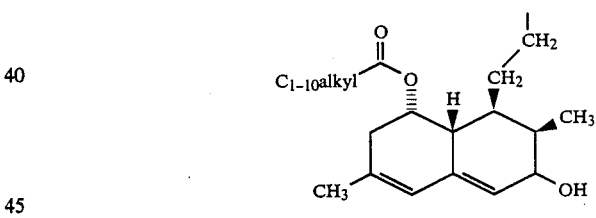

U.S. Pat. Nos. 4,537,859 and 4,448,979 also disclose hydroxy-containing compounds represented by the above general formula wherein R* is

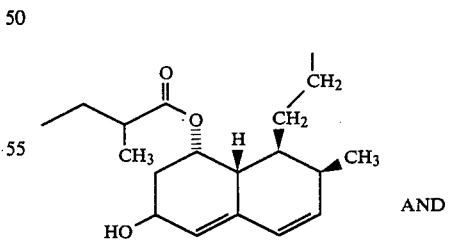

AND

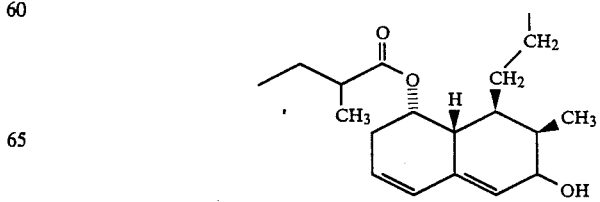

These compounds are prepared by the action of certain microorganisms on the corresponding non-hydroxylated substrates. One such organism described in U.S. Pat. No. 4,537,859 is of the genus Nocardia.

U.K. Patent No. 2,075,013 discloses hydroxy containing compounds represented by the above general formula wherein R* is:

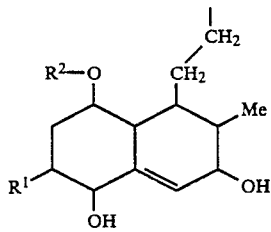

wherein $R^1$ is H or Me, and $R^2$ is H or acyl.

U.S. patent application Ser. No. 254,525 filed Oct. 6, 1988 discloses 6-substituted compounds of the above general formula wherein R* is:

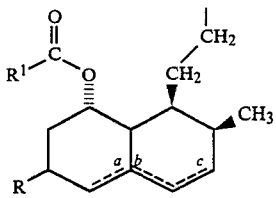

wherein R is $CH_2OH$,

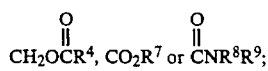

and $R^1$, $R^4$, $R^7$, $R^8$ and $R^9$ are broadly defined organic moieties.

U.S. Pat. Nos. 4,604,472 and 4,733,003 disclose compounds of the above formula wherein R* is:

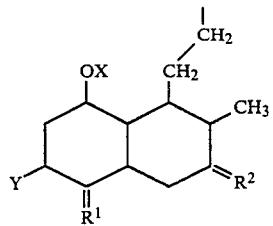

wherein X represents a hydrogen atom or a 2-methylbutyryl group, Y represents a hydrogen atom or a methyl group and $R^1$ and $R^2$ are the same or different and each represents an oxygen atom or a group of formula $=N-OR^3$ where $R^3$ is a hydrogen or alkyl moiety.

DETAILED DESCRIPTION OF THE INVENTION

This invention relates to HMG-CoA reductase inhibitors of structural formulae (I) and (II).

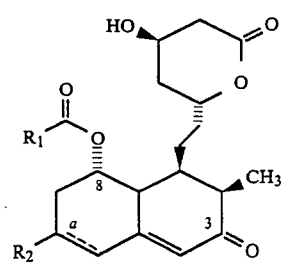

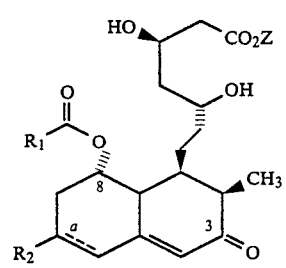

wherein:
$R^1$ is selected from:
(1) $C_{1-10}$ alkyl;
(2) substituted $C_{1-10}$ alkyl in which one or more substituent(s) is selected from
(a) halogen,
(b) hydroxy,
(c) $C_{1-10}$ alkoxy,
(d) $C_{1-5}$ alkoxycarbonyl,
(e) $C_{1-5}$ acyloxy,
(f) $C_{3-8}$ cycloalkyl,
(g) phenyl,
(h) substituted phenyl in which the substituents are X and Y,
(i) $C_{1-10}$ alkylS(O)$_n$ in which n is 0 to 2,
(j) $C_{3-8}$ cycloalkylS(O)$_n$,
(k) phenylS(O)$_n$,
(l) substituted phenylS(O)$_n$ in which the substituents are X and Y, and
(m) oxo;
(3) $C_{1-10}$ alkoxy;
(4) $C_{2-10}$ alkenyl;
(5) $C_{3-8}$ cycloalkyl;
(6) substituted $C_{3-8}$ cycloalkyl in which one substituent is selected from
(a) $C_{1-10}$ alkyl substituted $C_{1-10}$ alkyl in
(b) substituted $C_{1-10}$ alkyl in which the substituent is selected from
(i) halogen,
(ii) hydroxy,
(iii) $C_{1-10}$ alkoxy,
(iv) $C_{1-5}$ alkoxycarbonyl,
(v) $C_{1-5}$ acyloxy,
(vi) phenyl,
(vii) substituted phenyl in which the substituents are X and Y
(viii) $C_{1-10}$ alkylS(O)$_n$,
(ix) $C_{3-8}$ cycloalkylS(O)$_n$,
(x) phenylS(O)$_n$,
(xi) substituted phenylS(O)$_n$ in which the substituents are X and Y, and
(xii) oxo,
(c) $C_{1-10}$ alkylS(O)$_n$,
(d) $C_{3-8}$ cycloalkylS(O)$_n$,
(e) phenylS(O)$_n$, (f) substituted phenylS(O)$_n$ in which the substituents are X and Y,
(g) halogen.
(h) hydroxy,
(i) $C_{1-10}$ alkoxy,
(j) $C_{1-5}$ alkoxycarbonyl,
(k) $C_{1-5}$ acyloxy,
(l) ) phenyl, and
(m) substituted phenyl in which the substituents are X and Y;
(7) phenyl;
(8) substituted phenyl in which the substituents are X and Y,
(9) amino;
(10) $C_{1-5}$ alkylamino;
(11) di($C_{1-5}$ alkyl)amino;
(12) phenylamino;
(13) substituted phenylamino in which the substituents are X and Y;
(14) phenyl $C_{1-10}$ alkylamino;
(15) substituted phenyl $C_{1-10}$ alkylamino in which the substituents are X and Y;
(16) a member selected from
  (a) piperidinyl,
  (b) pyrrolidinyl,
  (c) piperazinyl,
  (d) morpholinyl, and
  (e) thiomorpholinyl; and
(17) R$_3$S in which R$_3$ is selected from
  (a) $C_{1-10}$ alkyl,
  (b) phenyl, and
  (c) substituted phenyl in which the substituents are X and Y,
R$_2$ is H, CH$_3$, or CH$_2$OH;
X and Y are independently selected from:
(a) OH,
(b) halogen,
(c) trifluoromethyl,
(d) $C_{1-3}$alkoxy,
(e) $C_{1-3}$alkylcarbonyloxy,
(f) phenylcarbonyloxy,
(g) $C_{1-3}$alkoxycarbonyl,
(h) phenyloxycarbonyl,
(i) hydrogen;
(j) $C_{1-5}$alkyl;
Z is selected from
(1) hydrogen;
(2) $C_{1-5}$alkyl;
(3) substituted $C_{1-5}$alkyl in which the substituent is selected from
  (a) phenyl,
  (b) dimethylamino, and
  (c) acetylamino, and
(4) 2,3-hydroxypropyl;
halogen is Cl or F;
a is a single bond or a double bond;
and pharmaceutically acceptable salts of the compound (II) in which Z is hydrogen.

Except where specifically defined to the contrary, the terms "alkyl", "alkenyl", "acyl" "aryloxy" and "alkoxy" include both the straight-chain and branched chain species of the term.

One embodiment of this invention is the class of compounds of formulae (I) and (II) wherein:
R$_1$ is selected from:
(1) $C_{1-10}$ alkyl;
(2) substituted $C_{1-10}$ alkyl in which one or more substituent(s) is selected from (a) halogen,
(b) hydroxy,
(c) $C_{1-10}$ alkoxy,
(d) $C_{1-5}$ alkoxycarbonyl,
(e) $C_{1-5}$ acyloxy,
(f) $C_{3-8}$ cycloalkyl,
(g) phenyl,
(h) substituted phenyl in which the substituents are X and Y, and
(i) oxo;
(3) $C_{3-8}$ cycloalkyl;
(4) substituted $C_{3-8}$ cycloalkyl in which one substituent is selected from
  (a) $C_{1-10}$ alkyl,
  (b) substituted $C_{1-10}$ alkyl in which the substituent is selected from
    (i) halogen,
    (ii) hydroxy,
    (iii) $C_{1-10}$ alkoxy
    (iv) $C_{1-5}$ acyloxy,
    (v) $C_{1-5}$ alkoxycarbonyl,
    (vi) phenyl,
    (vii) substituted phenyl in which the substituents are X and Y, and
    (viii) oxo,
  (c) halogen,
  (d) hydroxy,
  (e) $C_{1-10}$ alkoxy,
  (f) $C_{1-5}$ alkoxycarbonyl,
  (g) $C_{1-5}$ acyloxy,
  (h) phenyl,
  (i) substituted phenyl in which the substituents are X and Y;
(5) phenylamino;
(6) substituted phenylamino in which the substituents are X and Y;
(7) phenyl$C_{1-10}$alkylamino; and
(8) substituted phenyl $C_{1-10}$ alkylamino in which the substituents are X and Y,
X and Y are independently selected from:
(a) OH,
(b) F,
(c) trifluoromethyl,
(d) $C_{1-3}$ alkoxy,
(e) hydrogen,
(f) $C_{1-5}$ alkyl.

In one subclass are the compounds of formulae (I) and (II) wherein R$_1$ is $C_{1-10}$ alkyl.

Illustrating this subclass are those compounds of formulae (I) and (II) wherein:
R$_1$ is 2 butyl or 2 methyl 2-butyl; and
R$_2$ is H or CH$_3$.

Exemplifying this subclass are the following compounds:
(1) 6(R)-[2-[8(S)-(2-methylbutyryloxy) 2(S),6-dimethyl3-oxo-1,2,3,7,8,8a(R)-hexahydronaphthyl-1(S)ethyl]4(R) hydroxy 3,4,5,6-tetrahydro 2H-pyran-2-one;
(2) 6(R)-[2-[8(S)-(2,2-dimethylbutyryloxy) 2(S),6-dimethyl-3 oxo-1,2,3,7,8,8a(R)-hexahydronaphthyl-1(S)]ethyl]-4(R)-hydroxy-3,4,5,6-tetrahydro 2H-pyran-2 one;
(3) 6(R) [2-[8(S) (2-methylbutyryloxy) 2(S) methyl-3oxo-1,2,3,7,8,8a(R)-hexahydronaphthyl 1(S)]ethyl]-4(R) hydroxy-3,4,5,6 tetrahydro 2H-pyran-2-one;
(4) 6(R) [2 [8(S) (2,2-dimethylbutyryloxy)-2(S)-methyl 3-oxo-1,2,3,7,8,8a(R) -hexahydronaphthyl-1(S)]e- thyl]4(R)-hydroxy-3,4,5,6-tetrahydro 2H-pyran-2 one;

(5) 6(R) [2-[8(S) (2,2 dimethylbutyryloxy) 2(S),6(R)dimethyl-3 oxo-1,2,3,5,6,7,8,8a(R)-octahydro-naphthyl-1(S)]ethyl]-4(R)-hydroxy 3,4,5,6 tetrahydro-2H-pyran 2

(6) 6(R) [2 [8(S) (2,2-dimethylbutyryloxy)-2(S)-methyl-3 oxo 1,2,3,5,6,7,8,8a(R) octahydronaphthyl-1(S)]ethyl]-4(R) hydroxy-3,4,5,6-tetrahydro-2H-pyran-2-one.

(7) 6(R) [2-[8(S)-(2-methylbutyryloxy)-2(S),6(R)dimethyl-3-oxo-1,2,3,5,6,7,8,8a(R) octahydronaphthyl-1(S)]ethyl]4(R)-hydroxy 3,4,5,6 tetrahydro-2H-pyran-2-one (8) 6(R) [2 [8(S) (2-methylbutyryloxy) 2(S)-methyl-3-oxo-1,2,3,5,6,7,8,8a(R)-octahydronaphthyl-1(S)]ethyl]4(R) hydroxy 3,4,5,6-tetrahydro-2H-pyran-2-one.

The compounds of formulae (I) and (II) wherein $R_2$ is methyl and a is a double bond, may be prepared from lovastatin or simvastatin or its analogs having a 6 methyl group by one of the following microbiological procedures:

(a) adding the substrate to a growing culture of *Nocardia autotrophica* for a suitable incubation period followed by isolation, and derivatization if desired;

(b) collecting a culture of the bioconverting microorganism and contacting the collected cells with the substrate; or (c) preparing a cell free, enzyme-containing extract from the cells of the bioconverting microorganism and contacting this extract with the substrate.

Cultivation of the bioconverting microorganism of the genus Nocardia can be carried out by conventional means in a conventional culture medium containing nutrients well known for use with such microorganisms. Thus, as is well known, such culture media contain sources of assimilable carbon and of assimilable nitrogen and often inorganic salts. Examples of sources of assimilable carbon include glucose, sucrose, starch, glycerin, millet jelly, molasses and soybean oil. Examples of sources of assimilable nitrogen include soybean solids (including soybean meal and soybean flour), wheat germ, meat extracts, peptone, corn steep liquor, dried yeast and ammonium salts, such as ammonium sulphate. If required, inorganic salts, such as sodium chloride, potassium chloride, calcium carbonate or phosphates, may also be included. Also, if desired, other additives capable of promoting the production of hydroxylation enzymes may be employed in appropriate combinations. The particular cultivation technique is not critical to the process of the invention and any techniques conventionally used for the cultivation of microorganisms may equally be employed with the present invention. In general, of course, the techniques employed will be chosen having regard to industrial efficiency. Thus, liquid culture is generally preferred and the deep culture method is most convenient from the industrial point of view.

Cultivation will normally be carried out under aerobic conditions and at a temperature within the range from 20° to 37° C., more preferably from 26° to 28° C.

Method (a) is carried out by adding the substrate to the culture medium in the course of cultivation. The precise point during the cultivation at which the starting compound is added will vary depending upon the cultivation equipment, composition of the medium, temperature of the culture medium and other factors, but it is preferably at the time when the hydroxylation capacity of the microorganism begins to increase and this is usually 1 or 2 days after beginning cultivation of the microorganism. The amount of the substrate added is preferably from 0.01 to 5.0% by weight of the medium, more preferably from 0.05 to 0.5%, e.g., from 0.05 to 0.1% by weight. After addition of the substrate, cultivation is continued aerobically, normally at a temperature within the ranges proposed above. Cultivation is normally continued for a period of from 1 to 2 days after addition of the substrate.

In method (b), cultivation of the micro organism is first carried out under conditions such as to achieve its maximum hydroxylation capacity; this capacity usually reaches a maximum between 4 and 5 days after beginning the cultivation, although this period is variable, depending upon the nature and temperature of the medium, the species of micro organism and other factors. The hydroxylation capacity of the culture can be monitored by taking samples of the culture at suitable intervals, determining the hydroxylation capacity of the samples by contacting them with a substrate under standard conditions and determining the quantity of product obtained and plotting this capacity against time as a graph. When the hydroxylation capacity has reached its maximum point, cultivation is stopped and the microbial cells are collected. This may be achieved by subjecting the culture to centrifugal separation, filtration or similar known separation methods. The whole cells of the cultivating microorganism thus collected' preferably, are then washed with a suitable washing liquid, such as physiological saline or an appropriate buffer solution.

Contact of the collected cells of the microorganism of the genus Nocardia with the substrate is generally effected in an aqueous medium, for example in a phosphate buffer solution at a pH value of from 5 to 9. The reaction temperature is preferably within the range from 20° to 45° 403° C., more preferably from 25° to 30° C. The concentration of the substrate in the reaction medium is preferably within the range from 0.01 to 5.0% by weight. The time allowed for the reaction is preferably from 1 to 5 days, although this may vary depending upon the concentration of the substrate in the reaction mixture, the reaction temperature, the hydroxylation capacity of the micro organism (which may, of course, vary from species to species and will also, as explained above, depend upon the cultivation time) and other factors.

The cell free, enzyme-containing extract employed in method (c) may be obtained by breaking down the whole cells of the microorganism obtained as described in relation to method (b) by physical or chemical means, for example by grinding or ultrasonic treatment to provide a disintegrated cellular mass or by treatment with a surface active agent or an enzyme to produce a cellular solution. The resulting cell-free extract is then contacted with the substrate under the same conditions as are described above in relation to method (b).

The microorganism useful in the novel process of this invention is of the genus Nocardia. Of particular importance are the known strains of microorganism, Nocardia autotrophica, subspecies canberrica. ATCC 35203 of the culture MA 6181 and subspecies amethystina ATCC 35204 of the culture MA 6180 of the culture collection of Merck & Co., Inc., Rahway, N.J. A sample of the culture designated ATCC 35203 and ATCC 35204 is available in the permanent culture collection of the American Type Culture Collection at 12301 Parklawn Drive, Rockville, Md. 20852.

After completion of the conversion reaction by any of the above methods, the desired compound can be directly isolated, separated or purified by conventional means. For example, separation and purification can be effected by filtering the reaction mixture, extracting the resulting filtrate with a water-immiscible organic solvent (such as ethyl acetate), distilling the solvent from the extract, subjecting the resulting crude compound to column chromatography, (for example on silica gel or alumina) and eluting the column with an appropriate eluent, especially in an HPLC apparatus.

Where the acyl moiety of formulae (I) or (II) is other than 2-methylbutyryl or 2,2-dimethylbutyryl, the acyl moiety of lovastatin may be hydrolyzed and the hydroxyl group reesterified with an appropriate alkanoyl halide following the procedure in U.S. Pat. No. 4,444,784. The alkanoyl halide can be formed by standard transformations such as substitution with an alkyl halide or other appropriate electrophile at an acidic C H site on an available starting material. See for example U.S. Pat. No. 4,766,145 and allowed pending applications Ser. Nos. 205,406 and 205,407 filed June 10, 1988.

Starting material (1) wherein $R_2$ is $CH_2OH$ may be prepared following the procedures in copending application Ser. No. 254,525 filed Oct. 6, 1988.

The compounds of formulae (I) and (II) may also be prepared following the synthetic methodology in Scheme 1.

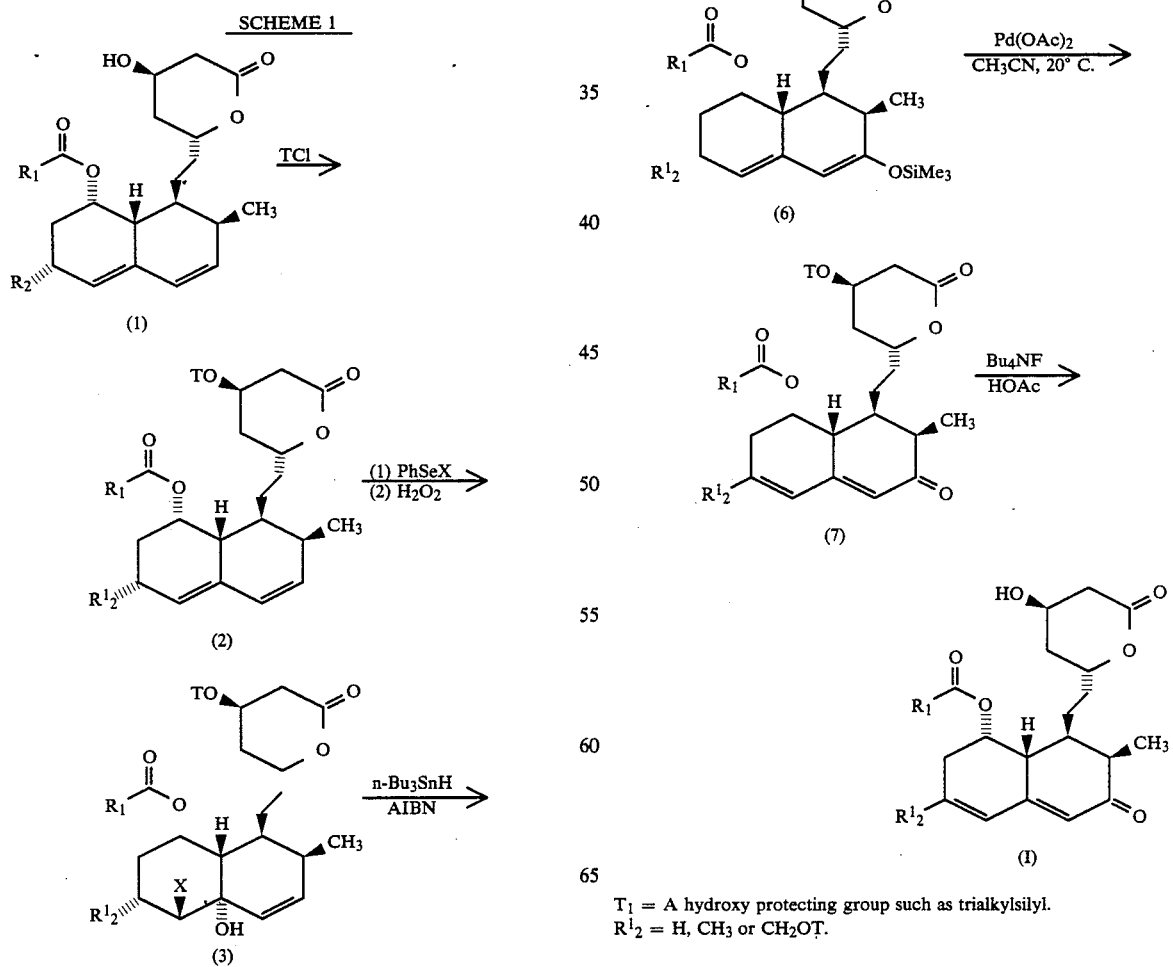

$T_1$ = A hydroxy protecting group such as trialkylsilyl.
$R^1_2$ = H, $CH_3$ or $CH_2OT$.

Starting material (1) is treated with a reagent suitable for protecting the alcohol group at the lactone 4-position. Examples of suitable reagents are trialkylsilyl chlorides, dialkylarylsilyl chlorides and dihydropyran.

The diene (2) is treated with a halogenating agent such as phenylselenyl chloride or bromide or phenylsulfinyl chloride, preferably phenylselenyl chloride, in an approximately equimolar ratio in an inert solvent at about −80° C., for approximately 20 minutes; illustrative of such inert solvents are methylene chloride, ether and the like. After a standard workup the product residue is dissolved in an ethereal solvent, chilled to about 0° C. and oxidized with an agent such as 30% hydrogen peroxide or a peroxy acid such as peroxybenzoic acid to yield a halohydrin analog (3).

Intermediate (3) is treated with a halide reducing agent such as a trialkyltin hydride or a triaryltin hydride, preferably tri-n butyltin hydride and a radical initiator such as azobisisobutyronitrile (AIBN) in an inert solvent such as benzene at a temperature between 70° C. and 100° C. preferably about 90° C. for 0.5 to 5 hours preferably 2 hours, to yield compound (4).

Compound (4) is treated with pyridinium chlorochromate (PCC) on aluminum oxide in toluene to yield the enone (5). Compound (5) is contacted with trimethylsilyl trifluoromethanesulfonate and an amine to yield the trimethylsilyl ether diene (6). Compound (6) is treated with palladium acetate in acetonitrile to form dienone (7). Hydroxyl protecting groups are removed by treatment with tetrabutyl ammonium fluoride and acetic acid in tetrahydrofuran to yield product (I).

Enone (5) can be converted to compounds of formula (I) wherein a is a single bond by treatment with tetrabutyl ammonium fluoride in acetic acid.

Alternatively the compounds of formulae (I) can be prepared following the synthetic outline of Scheme 2.

SCHEME 2

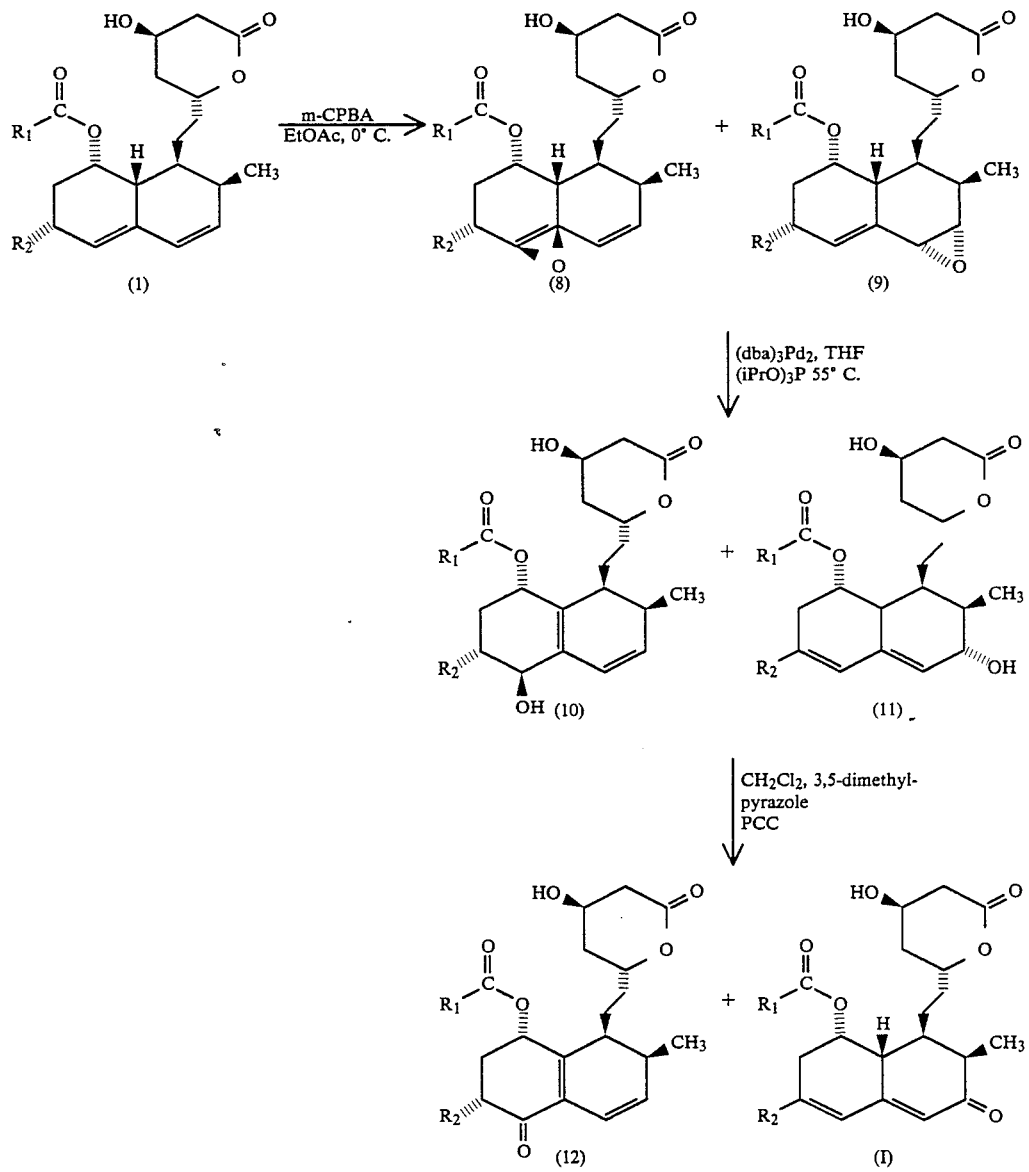

Diene starting material (1) is converted to epoxides (8) and (9) by treatment with m-chloroperoxybenzoic acid at about 0° C. The mixture of epoxides is then contacted with tris (dibenzylideneacetone) dipalladium(0) and triisopropoxy phosphine to yield the mixture of hydroxy dienes (10) and (11). This mixture is then oxidized with PCC attenuated with 3,5 dimethylpyrazole to yield 5 one compound (12) and product (I).

Enone (5) of Scheme 1 can also be formed from hydroxyl protected epoxide (9) or the mixture of epoxides (8) and (9) as shown below:

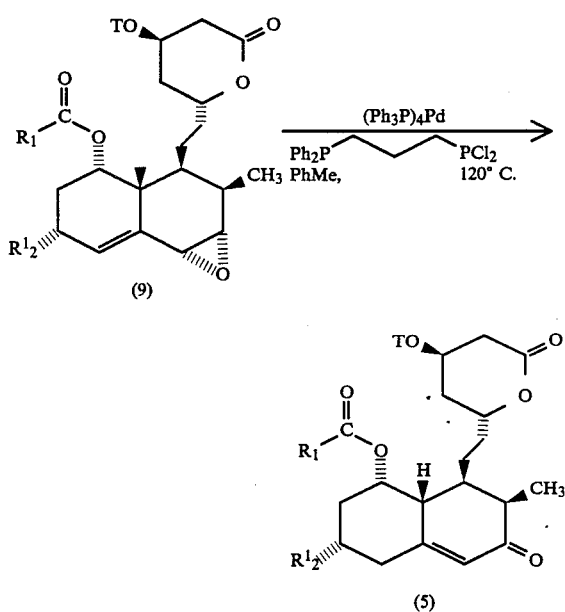

Compound (5) can then be employed in Scheme 1 to form product (1).

Where the reaction conditions of the above noted chemical transformations would be deleterious to the substituents in the 8-acyloxy moiety, the acetoxy group can be employed as a protecting group which after the elaboration elsewhere in the molecule can be removed by hydrolysis to give the 8 hydroxy derivative which then can be acylated according to the general procedures described in U.S. Pat. No. 4,661,483.

Where the product formed by the above described synthetic: pathways is not the desired form of that compound, then that product may be subjected to one or more further reactions such as hydrolysis, disilylation, salification, esterification, acylation, ammonolysis or lactonizaton by conventional methods.

Preferred metal salts are salts with alkali metals, such as sodium or potassium, salts with alkaline earth metals, such as calcium or magnesium, or salts with other metals such as aluminum, iron, zinc, copper, nickel or cobalt, of which the alkali metal, alkaline earth metal, and aluminum salts are preferred, the sodium, calcium and aluminum salts being most preferred.

Preferred amino acids to form amino acid salts are basic amino acids, such as arginine, lysine, $\alpha,\beta$-diaminobutyric acid or ornithine.

Preferred amines to form amine salts include dibenzylamine, ethylenediamine, morpholine, and tris(hydroxymethyl)aminomethane. Also preferrred is ammonia to form the ammonium salt.

Esters are preferably the alkyl esters, such as the methyl, ethyl, propyl, isopropyl, butyl, isobutyl, or pentyl esters, of which the methyl ester is preferred. However, other esters such as phenyl-$C_{1-5}$alkyl, dimethylamino-$C_{1-5}$alkyl, or acetylamino-$C_{1-5}$alkyl may be employed if desired.

Metal salts of the carboxylic acids of formula (II) may be obtained by contacting a hydroxide or carbonate with the carboxylic acid of formula (II). The aqueous solvent employed is preferably water, or it may be a mixture of water with an organic solvent, preferably an alcohol (such as methanol or ethanol), a ketone (such as acetone), an aliphatic hydrocarbon (such as hexane) or an ester (such as ethyl acetate). It is preferred to use a mixture of a hydrophilic organic solvent with water. Such reactions are normally conducted at ambient temperature but they may, if desired, be conducted with heating or cooling.

Amine salts of the carboxylic acids of formula (II) may be obtained by contacting an amine in an aqueous solvent with the carboxylic acid of formula (II). Suitable aqueous solvents include water and mixtures of water with alcohols (such as methanol or ethanol), ethers (such as diethyl ether and tetrahydrofuran), nitriles (such as acetonitrile) or ketones (such as acetone); it is preferred to use aqueous acetone as the solvent for this reaction. The reaction is preferably carried out at a temperature of ambient or below, more preferably a temperature of from 5° to 10° C. The reaction immediately goes to completion. Alternatively, a metal salt of the carboxylic acid of formula (II) (which may have been obtained as described above) can be dissolved in an aqueous solvent, after which a mineral acid salt (for example the hydrochloride) of the desired amine is added, employing the same reaction conditions as when the amine itself is reacted with the carboxylic acid of formula (II) and the desired product is then obtained by metathesis.

Amino acid salts of the carboxylic acids of formula (II) may be obtained by contacting an amino acid in aqueous solution with the carboxylic acid of formula (II). Suitable aqueous solvents include water and mixtures of water with alcohols (such as methanol or ethanol) or ethers (such as tetrahydrofuran).

Esters, preferably alkyl esters, of the carboxylic acids of formula (II) may be obtained by contacting the carboxylic acid of formula (II) with an appropriate alcohol, preferably in the presence of an acid catalyst, for example a mineral acid (such as hydrochloric acid or sulphuric acid), a Lewis acid (for example boron trifluoride) or an acidic ion exchange resin. The solvent employed for this reaction is not critical, provided that it does not adversely affect the reaction; suitable solvents include the alcohol itself, benzene, chloroform, ethers and the like. Alternatively, the desired product may be obtained by contacting the carboxylic acid of formula (II) with a diazoalkane, in which the alkane moiety may be substituted or unsubstituted. This reaction is usually effected by contacting the acid with an ethereal solution of the diazoalkane. As a further alternative, the ester may be obtained by contacting a metal salt of the carboxylic acid of formula (II) with a halide, preferably an alkyl halide, in a suitable solvent; preferred solvents include dimethylformamide, tetrahydrofuran, dimethylsulfoxide and acetone. Finally, esters may also be obtained from the lactone of formula (I) by reaction with an appropriate alkoxide in an absolute alkanol. All of the reactions for producing esters are preferably effected at about ambient temperature, but, if required by the nature of the reaction system, the reactions may be conducted with heating or cooling.

Lactones of the carboxylic acids of formula (I) may be obtained by lactonizing the carboxylic acids of formula (II) under ordinary conditions known to one skilled in the art.

The intrinsic HMG-CoA reductase inhibition activity of the claimed compounds is measured in the in vitro Protocol published in *J. Med. Chem.*, 28, p. 347-358 (1985).

Representative of the intrinsic HMG-CoA reductase inhibitory activities of the claimed compounds is the relative potency of 6(R)-[2-[8(S)-(2,2-dimethylbutyryloxy)-2(S),6-dimethyl-3-oxo-1,2,3,7,8,8a(R)-hexahydronaphthyl-1(S)]ethyl]-4(R)-hydroxy-3,4,5,6-tetrahydro-2H-pyran-2-one which exhibited an $IC_{50}$ value of 2 ng/ml when compared to an $IC_{50}$ value of 4.2 ng/ml for simvastatin. Compound 6(R)-[2-[8(S)-(2,2-dimethylbutyryloxy)-2(S), 6(R)-dimethyl-3-oxo-1,2,3,5,6,7,8,8a(R)-octahydro-naphthyl-1(S)]ethyl]-4(R)-hydroxy-3,4,5,6-tetrahydro-2H-pyran-2-one; exhibited an $IC_{50}$ of 20 ng/ml.

The compounds of this invention are useful as antihypercholesterolemic agents for the treatment of arteriosclerosis, hyperlipidemia, familial hypercholesterolemia and the like diseases in humans. They may be administered orally or parenterally in the form of a capsule, a tablet, an injectable preparation or the like. It is usually desirable to use the oral route. Doses may be varied, depending on the age, severity, body weight and other conditions of human patients but daily dosage for adults is within a range of from about 2 mg to 2000 mg (preferably 10 to 100 mg) which may be given in two to four divided doses. Higher doses may be favorably employed as required.

The compounds of this invention may also be coadministered with pharmaceutically acceptable nontoxic cationic polymers capable of binding bile acids in a non-reabsorbable form in the gastro intestinal tract. Examples of such polymers include cholestyramine, colestipol and poly[methyl-(3-trimethylaminopropyl-)imino-trimethylene dihalide]. The relative amounts of the compounds of this invention and these polymers is between 1:100 and 1:15,000.

Included within the scope of this invention is the method of treating arteriosclerosis, familial hypercholesterolemia or hyperlipidemia which comprises administering to a subject in need of such treatment a nontoxic, therapeutically effective amount of the compounds of formulae (I) or (II) or pharmaceutical compositions thereof.

The following examples illustrate the preparation of the compounds of the formulae (I) and (II) and their incorporation into pharmaceutical compositions and as such are not to be considered as limiting the invention set forth in the claims appended hereto.

EXAMPLE 1

Preparation of 6(R)-[2-[8(S)-(2,2-dimethylbutyryloxy)-2(S),6-dimethyl-3-oxo-1,2,3,7,8,8a(R)-hexahydronaphthyl-1(S)]ethyl]-4(R)-hydroxy-3,4,5,6-tetrahydro-2H-pyran-2-one Utilizing the general procedure for the bioconversion of sodium salt of 7-[1,2,6,7,8,8a(R)-hexahydro-2(S),6(R)-dimethyl-8(S)-(2,2-dimethylbutyryloxy)-1(S)-naphthyl]-3(R),5(R)-dihydroxyheptanoic acid as described in co-pending patent application Ser. No. 254,525, filed Oct. 6, 1988 the above titled compound was isolated as a minor product.

The following media are utilized in the bioconversion reactions described below:

| | Grams per liter distilled water |
|---|---|
| Medium A | |
| Yeast extract | 4.0 |
| Malt extract | 10.0 |
| Nutrient broth | 4.0 |
| Dextrose | 4.0 |
| pH 7.4 | |
| Medium sterilized for 20 min. at 121° C. | |
| Medium B | |
| Dextrose | 10.0 |
| Polypeptone | 2.0 |
| Meat extract | 1.0 |
| Corn steep liquor | 3.0 |
| pH 7.0 | |
| Medium sterilized for 20 min. at 121° C. | |

I. Culture Conditions and Bioconversion

A lyophilized tube of *Nocardia autotrophica* subsp. *canberrica* ATCC 35204 (MA-6180) was used to inoculate 18×175 agar slants (Medium A) which were incubated at 27° C. for 7 days. The slant culture was washed with 5 ml of sterile medium B and transferred to a 250 ml flask containing 50 ml of sterile medium B. This first stage seed was grown at 27° C. on a 220 rpm shaker and, after 24 hours, 2 ml was transferred to another flask of sterile medium B.

Grown under the above conditions, the second seed was used to start the bioconversion culture: 20 ml of the seed culture was placed in 400 ml of sterile medium B in a 2 L flask. After the culture had grown for 24 hours, 80 mg of the sodium salt of 7-[1,2,6,7,8,8a(R)-hexahydro-2(S),6(R)-dimethyl-8(S)-(2,2-dimethylbutyryloxy)-1(S)-naphthyl]-3(R),5(R)-dihydroxyheptanoic acid was added to each flask. The incubation was continued for 28 hours or until no 7-[1,2,6,7,8,8a(R)-hexahydro-2(S),6(R)-dimethyl-8(S)-(2,2-dimethylbutyryloxy)-1(S)-naphthyl]-3(R),5(R)-dihydroxyheptanoic acid could be detected by HPLC. The whole broth was clarified by centrifugation followed by filtration through Whatman No. 2 filter paper.

II. HPLC Methods

Aliquots of whole broth could be analyzed for 7-[1,2,6,7,8,8a(R)-hexahydro-2(S),6(R)-dimethyl-8(S)-(2,2-dimethylbutyryloxy)-1(S)-naphthyl]-3(R),5(R)-dihydroxyheptanoic acid derivatives by HPLC. Filtered broth could be injected directly (10 to 20 μl) or after dilution with methanol. The compounds were separated on reverse phase columns utilizing a gradient from 35 to 45 percent aqueous acetonitrile at flow rates ranging between 1 and 3 ml/min. Addition of glacial acetic acid or $H_3PO_4$ (0.1 ml/L mobile phase) was required for the separation of the free acids. Derivatives of 7-[1,2,6,7,8,8a(R)-hexahydro-2(S),6(R)-dimethyl-8(S)-(2,2-dimethylbutyryloxy)-1(S)-naphthyl]-3-(R),5(R)-dihydroxyheptanoic acid were detected by monitoring the absorbance at 238 nm, as well as the absorbance ratio of 238 nm/228 nm. The desired products, 6(R)-[2-[8(S)-(2-alkylacyloxy)-2(S),6-dimethyl-3-oxo-1,2,3,7,8,8a(R)-hexahydronaphthyl-1(S)]ethyl]-4(R)-hydroxy-3,4,5,6-tetrahydro-2H-pyran-2-one, were detected by monitoring the absorbance at 293 nm.

III.
6(R)-[2-[8(S)-(2,2-dimethylbutyryloxy)-2(S),6-dimethyl-3-oxo-1,2,3,7,8,8a(R)-hexahydronaphthyl-1(S)]-ethyl]-4(R)-hydroxy-3,4,5,6-tetrahydro-2H-pyran-2-one Following the general procedure described above, the pH of the whole broth from the bio conversion of twenty kilograms of the sodium salt of 7-[1,2,6,7,8,8a(R)-hexahydro-2(S),6(R)-dimethyl-8(S)-(2,2-dimethylbutyryloxy)-1(S)-naphthyl]-3(R),5(R)-dihydroxyheptanoic acid (12,700 liters) was adjusted to 4.0 with 2N sulfuric acid and was then extracted with ethyl acetate (2×4500 l.). The whole broth extraction was followed by an extraction of the ethyl acetate solution into 1N sodium bicarbonate (20% by volume) and the aqueous extract was then washed with ethyl acetate. To the aqueous extract was then added methylisobutylketone (MIBK, 570 l.) and the pH of the aqueous phase adjusted to 3.1 using 7.2N sulfuric acid. The MIBK extract of the acidified aqueous phase was then separated from the aqueous phase which was then extracted with a second time MIBK (570 l.). The MIBK extracts were combined, filtered through diatomaceous earth, azeotropically dried and concentrated in vacuo to 870 liters. The MIBK solution was heated to 95° C., and then treated with trifluoroacetic acid (0.9 l.) in MIBK (23 l.).

After about 15 minutes, the mixture was cooled to 25° C. and washed successively with 1N sodium bicarbonate (0.5 volumes) and water (2×0.5 volumes). The organic phase was concentrated in vacuo and the residue dissolved in acetonitrile, which was then diluted to 30% acetonitrile using 0.02M phosphate buffer at pH=7. Aliquots ($\frac{1}{3}$) which contain approximately 700 gm. of 6(R)-[2-[8(S)-(2,2-dimethylbutyryloxy)-6-hydroxymethyl-2(S)-methyl-1,2,6,7,8,8a(R)-hexahydronaphthyl-1(S)]ethyl]-4(R)-hydroxy-3,4,5,6-tetrahydro-2H-pyran-2-one were chromatographed over an SP-207 (300 l, brominated copolymer of styrene and divinylbenzene, Mitsubishi Co.) column. Elution with acetonitrile/buffer (30%, 37%, 47%, 57%,) and acetonitrile/water (67%) gave the above titled product and the 6-hydroxymethyl compound as a mixture. The desired product may be further purified by removing most of the 6-hydroxymethyl compound by crystallization by dissolving the mixture in isopropyl acetate (IPAC) or methyl-t-butyl ether (MTBE) and then adding the solution to a non-polar solvent (n-heptane, cyclohexane or petroleum ether).

IV. Isolation of 6(R)-[2-[8(S)-(2,2-dimethylbutyryloxy)-2(S),6-dimethyl-3-oxo-1,2,3,7,8,8a(R)-hexahydronaphthyl-1(S)ethyl]-4(R)-hydroxy-3,4,5,6-tetrahydro-2H-pyran-2-one The crystallization mother liquors from Step III were concentrated to an oil and then dissolved in toluene:methanol:acetonitrile (8:1:1, V:V:V) to a final volume of 100 ml. This solution was charged to a 10 liter column of Sephadex LH 20 (Pharmacia Inc.) equilibrated with hexane:toluene:methanol (3:1:1, V:V:V) and eluted with this solvent at a flow rate of 100 ml/min.

The desired compound eluted between 11 and 14 column volumes and the rich cut eluant was concentrated to a solid. The product was further purified by preparative reverse phase hplc on a $C_{18}$ column (21.4 mm ID×30 cm) eluted with a linear gradient starting 10 minutes after injection from 25% acetonitrile in water to 75% acetonitrile in water over 40 minutes at a flow rate of 10 ml/min. The fractions containing the desired product (eluting at 29 minutes) were combined and concentrated to yield about 400 mg. of the desired product in crystalline form.

$^{13}C$ NMR Data ($CD_2Cl_2$, $\delta_c=53.8$ ppm)

| ppm | ppm | ppm |
|---|---|---|
| 9.4 | 36.5 | 67.0 |
| 10.6 | 36.8 | 76.0 |
| 24.1 | 37.7 | 123.1 |
| 24.3 | 39.0 | 124.5 |
| 24.4 | 39.6 | 144.3 |
| 24.9 | 42.7 | 154.9 |
| 32.9 | 43.3 | 170.2 |
| 33.4 | 63.1 | 177.6 |
| | | 203.4 |

MS analysis showed a weak $M^+$ ion at m/z 432 and fragment ions at m/z 316 and 173 (base).

UV spectrum exhibited a $\lambda max=290$ nm, with $\epsilon=21,900$.

In a similar fashion *Nocardia autotrophica* subsp. *canberrica* ATCC 35203 (MA6181) was utilized in the bioconversion reaction with the sodium salt of 7-[1,2,6,7,8,8a(R)-hexahydro-2(S),6(R)-dimethyl-8(S)-(2,2-dimethylbutyryloxy)-1(S)-naphthyl]-3(R),5(R)-dihydroxyheptanoic acid to afford the desired products.

Additionally, the sodium salt of 7-[1,2,6,7,8,8a(R)-hexahydro-2(S),6(R)-dimethyl-8(S)-(2-methylbutyryloxy)-1(S)-naphthyl]-3(R),5(R)-dihydroxyheptanoic acid, the sodium salt of ring opened lovastatin, was subjected to analogous bioconversion reactions utilizing both *N. autotrophic* subsp. *amethystina* ATCC 35204 (MA6180) and *N. autotrophic* subsp. *canberrica* ATCC 35203 (MA6181) to afford 6(R)-[2-[8(S)-(2-methylbutyryloxy)-2(S),6-dimethyl-3-oxo-1,2,3,7,8,8a(R)-hexahydronaphthyl-1(S)]-ethyl]-4(R)-hydroxy-3,4,5,6-tetrahydro-2H-pyran-2-one.

EXAMPLE 2

Preparation of 6(R)-[2-[8(S)-(2,2-dimethylbutyryloxy)-2(S),6-dimethyl-3-oxo-1,2,3,5,6,7,8,8a(R) octahydronaphthyl-1(S)]-ethyl]-4(R)-hydroxy-3,4,5,6-tetrahydro-2H-pyran-2-one Thirty milligrams of the dieneone product of example 1 ($R_1=2$-methyl-2-butyl, a=double bond), dissolved in 3 ml of ethyl acetate, was hydrogenated (1 atm $H_2$, room temperature) over 6 mg of 10% palladium on carbon for 30 hours. Removal of the catalyst by filtration and evaporation of the solvent afforded the title compound. IR(film): 1718 $cm^{-1}$, 665 $cm^{-1}$. MS(EI) m/z 434 ($M^+$).

EXAMPLE 3

Preparation of 6(R)-[2-[8(S)-(2,2-dimethylbutyryloxy)-(S)-2(S),6-dimethyl-3-oxo-1,2,3,7,8,8a(R)-hexahydronaphthyl-1(S)]-ethyl]-4(R)-hydroxy-3,4,5,6-tetrahydro-2H-pyran-2-one (a)

6(R)-[2-[8(S)-(2,2-Dimethylbutyryloxy)-2(S),6(R)-dimethyl-1,2,6,7,8,8a(R)-hexahydronaphthyl-1(S)]-ethyl]-4(R)-(t-butyldimethylsilyloxy)-3,4,5,6-tetrahydro-2H-pyran-2-one (2')

Tert-Butyldimethylsilyl chloride (8 g, 52 mmol) was added to a stirred solution of 6(R)-[2-[8(S)-(2,2-Dimethylbutyryloxy)-2(S),6(R)-dimethyl-1,2,6,7,8,8a(R)-hexahydronaphthyl-1(S)]ethyl]-4(R)-hydroxy-3,4,5,6-tetrahydro-2H-pyran-2-one (20 g, 48 mmol) and imidazole (6.8 g, 0.1 mol) in DMF (150 mL) at 0° C. The resulting mixture was stirred at 0° C. for 5 minutes, then warmed to room temperature and stirred for 5 hours. TLC analysis of an aliquot indicated that the reaction was complete. The reaction mixture was poured into cold water and extracted with ether. The ethereal extract was washed with dilute hydrochloric acid, water and 5% sodium bicarbonate solution. After drying over $MgSO_4$, the organic extract was filtered and the filtrate was concentrated in vacuo to afford the desired product as a colorless, viscous oil: NMR ($CDCl_3$) δ 0.84 (3H, t, J=7 Hz), 0.89 (3H, d, J=7 Hz), 0.90 (9H,s), 1.09 (3H, d, J=7 Hz), 1.11 (3H, s), 1.12 (3H, s), 4.30 (H, m), 4.60 (H, m), 5.33 (H, m), 5.51 (H, m), 5.77 (H, d of d, J=10, 6 Hz), 5.98 (H, d, J=10 Hz). (b) 6(R)-[2-[5(S)-Chloro-4a(S)-hydroxy-8(S)-(2,2-dimethylbutyryloxy)-2(S),6(R)-dimethyl-1,2,4a,5,6,7,8,8a(S)-octahydronaphthyl-1(S)]ethyl]-4(R)-(t-butyldimethylsilyloxy)-3,4,5,6-tetrahydro-2H-pyran-2-one (3')

A solution of phenylselenyl chloride (10 g, 52 mmol) in methylene chloride (50 mL) was added dropwise to a stirred solution of compound 2' (25.2 g, 48 mmol) in methylene chloride (350 mL) cooled in a dry ice/ipropanol bath (−78° C.). The resulting mixture was stirred at −78° C. for 20 minutes, poured into cold water (300 mL) and extracted with ether twice (400 mL, then 150 mL). The combined extracts were dried ($MgSO_4$), filtered and concentrated to afford an oily residue which was dissolved in tetrahydrofuran (300 mL). This solution was chilled in an ice bath (0° C.), and 30% hydrogen peroxide (15 mL) was added. The resulting mixture was stirred at 0° C. for 5 minutes, then warmed to room temperature and stirring continued for 1 hour. The reaction mixture was poured into cold water and extracted with chloroform three times (400 mL, then 2×100 mL). The combined extracts were dried ($MgSO_4$), filtered and concentrated to yield a residue which was purified by flash chromatography on a silica gel column. Elution with hexane:ethyl acetate (5:1/v:v) removed the impurities. Further elution with hexane:ethyl acetate (4:1/v:v) provided the title compound as a pale yellow gum which later solidified on standing: mp 117°-8° C., NMR ($CDCl_3$) δ 0.075 (3H, s), 0.08 (3H, s), 0.85 (3H, t, J=7 Hz), 0.88 (9H, s), 0.89 (3H, d, J=7 Hz), 1.15 (3H, s), 1.16 (3H, s), 1.32 (3H, d, J=7 Hz), 1.58 (2H, q, J=7 Hz), 3.39 (H, s), 4.05 (H, bs), 4.30 (H, m), 4.60 (H, m), 5.32 (H, m), 5.59 (H, d, J=11 Hz), 5.79 (H, d of d, J=11, 6 Hz).

Anal. Calcd. for $C_{31}H_{53}ClO_6Si$: C, 63.61; H, 9.13. Found: C, 63.80; H, 9.04.

(c)
6(R)-[2-[4a(S)-hydroxy-8(S)-(2,2-dimethylbutyryloxy)-2(S),6(R)-dimethyl-1,2,4a,5,6,7,8,8a(S)-octahydronaphthyl-1(S)]ethyl]-4(R)-(t-butyldimethylsilyloxy)-3,4,5,6-tetrahydro-2H-pyran-2-one (4')

Tributyltin hydride (7.06 ml, 26.25 mmol) and azobisisobutyronitrile (AIBN) (0.82 g, 5.0 mmol) were added to a magnetically stirred solution of chlorohydrin 3' (8.78 g, 15 mmol) in benzene (100 ml). The resulting solution was refluxed for 2 hours. cooled and concentrated in vacuo to a viscous yellow oil which was stirred with pet ether (200 ml) at −15° C. (ice/acetone bath) to provide 4' as a fluffy, colorless solid (6.9 g, mp 97°-9° C.). The filtrate was extracted with $CH_3CN$ (4×50 ml) to remove all of the product contained in the pet ether. The $CH_3CN$ extracts were combined and concentrated to a colorless oil which was purified by flash chromatography on a silica gel column. Elution with ethyl acetone/hexane (1:3/v:v) gave a colorless solid (1.0 g) which was stirred in pet ether (25 ml) at 0° C. to remove some tin residues. The mixture was filtered to provide the product 4' as a colorless solid. M.P. 103°-4° C., nmr ($CDCl_3$) δ 0.07 (3H, s), 0.08 (3H, s), 0.88 (9H, s), 1.15 (3H, s), 1.16 (3H, s), 1.20 (3H, d, J=7 Hz), 2.78 (H, s), 4.28 (H, m), 4.58 (H, m), 5.30 (H, m), 5.58 (H, d, J=10 Hz), 5.67 (H, dd, J=10, 5 Hz).

Anal. Calcd. for $C_{31}H_{54}O_6Si$: C, 67.59; H, 9.88. Found: C, 67.20; H, 9.99.

(d)
6R-[2-[3-oxo-8(S)-(2,2-dimethylbutyryloxy)-2(S)6-(R)-dimethyl-1,2,3,5,6,7,8,8a-octahydronaphthyl-1(S)]-ethyl]-4(R)-(t-butyldimethylsilyloxy)-3,4,5,6-tetrahydro-2H-pyran-2-one (5')

7.2 g (12 mmol) of compound (4') was combined with 60 ml of toluene and 42 g of pyridinum chlorochromate/aluminum oxide. The mixture was stirred and heated on a steam bath for 20 minutes after which time tlc showed the reaction to be complete. The mixture was cooled, filtered and the solids washed with warm toluene (4×50 ml). The solvent was evaporated to yield an amber gum. Nmr ($CDCl_3$) δ 0.073 (3H, s), 0.079 (3H, s), 0.804 (3H, t, J=7 Hz), 0.881 (9H, s), 1.026 (2H, d, J=6 Hz), 1.036 (3H, d, J=6 Hz), 1.10 (6H, br s), 2.55 2.66 (3H, m), 4.276 (H, m), 4.588 (H, m) 5.42 (H, m), 5.910 (H, d, J=1.5 Hz)

(e)
6(R)-[2-[8(S)-(2,2-dimethylbutyryloxy)-2(S),6(R)-dimethyl-3-(trimethylsilyloxy)-1,2,6,7,8,8a(R)-hexahydro-1(S)]ethyl]-4(R)-(t-butyldimethylsilyloxy)-3,4,5,6-tetrahydro-2H-pyran-2-one (6')

The amber gum product of Step 3d was dissolved in methylene chloride and cooled to 0° C. under argon. The solution was treated with triethylamine (7.2 ml, 50 mmol) followed by slow addition of trimethylsilyl trifluoromethanesulfonate (5.4 ml, 28 mmol) while maintaining the temperature below 3° C. After stirring at 0° C. for 15 minutes (tlc showed the reaction to be complete by 5 minutes) the dark solution was diluted with methylene chloride (100 ml), washed with sat. $NaHCO_3$ (100 ml), dried and the solvent evaporated.

(f)
6(R)-[2-[8(S)-(2,2-dimethylbutyryloxy)-2(S),6-dimethyl-3-oxo-1,2,3,7,8,8a(R)-hexahydronaphthyl-1(S)]ethyl]-4(R)-(t-butyldimethylsilyloxy)-3,4,5,6-tetrahydro-2H-ryran-2-one (7')

The dark-amber residue of Step (3e) was dissolved in acetonitrile/tetrahydrofuran. Palladium (II) acetate (3.0 g, 13.0 mmol) was added to the mixture and the mixture stirred at room temperature for 22 hours, at which time tlc showed the reaction to be complete. The mixture was filtered through a 3 cm pad, of silica gel and then washed with ethyl acetate (150 ml), and the solvent evaporated. Nmr ($CDCl_3$) δ 0.076 (3H, s) 0.082 (3H, s) 0.752 (3H, t, J=7 Hz) 0.883 (9H, s) 1.033 (3H, d, J=7 Hz) 1.059 (3H, s) 1.065 (3H, s) 1.804 (3H, s) 4.295 (H, m) 4.606 (H, m) 5.408 (H, m) 5.781 (H, br s), 6.136 (H, br s).

(g) 6(R)-[2-[8(S)-(2,2-dimethylbutyryloxy)-2(S),6-dimethyl-3-oxo-1,2,3,7,8,8a(R)-hexahydronaphthyl-1(S)]ethyl]-4(R)-hydroxy-3,4,5,6-tetrahydro-2H-furan one (I)

The dark brown gum of Step (3f) was dissolved in tetrahydrofuran, and to this was added a mixture of tetra n-butyl ammonium fluoride (30 ml) and acetic acid (5.6 ml). The combined mixture was stirred at 50° C. for 4 hours, cooled, diluted with ethyl ether (400 ml) washed with water (5×100 ml), dried and the solvent evaporated. The residue solidified to a brown mass. The brown mass was chromatographed on a 50 mm LP column using hexane-ethylacetate, 1:1 for the first 10 fractions (25 ml fractions) then 1:2 for 11. then 1:4. The titled product was found in fractions 25–53, m.p. 160°–174° C. This chromatographed product was then recrystallized from ethyl acetate (30 ml) hexane (30 ml) After drying at 60° C. for 2 hours under a vacuum the titled product was obtained with M.P. 179°–180° C. Nmr (CDCl$_3$) δ 0.758 (3H, t, J=7.4 Hz) 1.035 (3H, d, J=7.4 Hz) 1.063 (3H, s), 1.069 (3H, s), 1.867 (3H, s), 2.63 (H, ddd, J=1.47, 3.64, 12.6 Hz), 2.749 (H, dd, 4.94, 12,6 Hz) 4.398 (H, m), 4.645 (H, m), 5.424 (H, m), 5.781 (H, brs), 6.138 (H, brs)

Anal. Calcd. for $C_{25}H_{36}O_6$: C, 69.42; H, 8.39 Found: C, 69.73; H, 8.54.

EXAMPLE 4

Preparation of 6(R)-[2-[3-oxo-8(S)-(2,2-dimethylbutyryloxy)-2(S),6(R)-dimethyl-1,2,3,5,6,7,8,8a-octahydronaphthyl-1(S)]ethyl]-4(R)-hydroxy-2,4,5,6-tetrahydro-2H-pyran-2-one A solution of compound (5') (500 mg, 0.9 mmol) of example 3 in acetic acid (42 ml) and water (15 ml) was heated at 70° C. for 3 hours. After cooling, the reaction mixture was diluted with water and extracted with ether. The ethanol extract was washed with water five times, then washed with aqueous sodium bicarbonate and brine. After drying and filtration, the filtrate was evaporated to afford a residue which was purified by flash chromatography on silica gel column. Elution of the column with 30% of acetone in methylene chloride gave the title compound as a solid: mp 117°–8° C.; nmr (CDCl$_3$) δ 0.80 (3H, t, J=7 Hz), 1.02 (3H, d, J=7 Hz), 1.04 (3H, d, J=7 Hz), 1.10 (6H, s), 2.64 (H, m of d, J=18 Hz), 2.72 (H, d of d, J=18, 4 Hz), 4.3H (H, m), 4.65 (H, m), 5.44 (H, m), 5.92 (H, bs).

Anal. Calcd. for $C_{25}H_{38}O_6$: C, 69.09; H, 8.81 Found: C, 68.85; H, 8.65.

EXAMPLE 5–9

Following the procedure of Example 3 and substituting an equivalent amount of reactant (A) for simvastatin in step (a), the product (B) is formed.

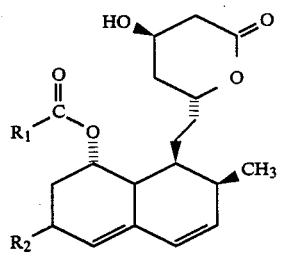

A

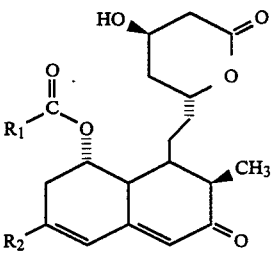

B

Example

5 R$_1$=2-butyl, R$_2$=CH$_3$;
6 R$_1$=2-butyl, R$_2$=H,
7 R$_1$=2-methyl-2-butyl, R$_2$=H;
8 R$_1$=2-methyl-2-butyl, R$_2$=CH$_2$OH;
9 R$_1$=2-butyl, R$_2$=CH$_2$OH.

EXAMPLE 10

Preparation of Ammonium Salts of Compounds II

The lactone (1.0 mmol) from Example 1 is dissolved with stirring in 0.1N NaOH (1.1 mmol) at ambient temperature. The resulting solution is cooled and acidified by the dropwise addition of 1N HCl. The resulting mixture is extracted with diethyl ether and the extract washed with brine and dried (MgSO$_4$). The MgSO$_4$ is removed by filtration and the filtrate saturated with ammonia (gas) to give a gum which solidified to provide the ammonium salt.

EXAMPLE 11

Preparation of Alkali and Alkaline Earth Salts of Compounds II

To a solution of 42 mg of lactone from Example 1 in 2 ml of ethanol is added 1 ml of aqueous NaOH (1 equivalent). After one hour at room temperature, the mixture is taken to dryness in vacuo to yield the desired sodium salt.

In like manner, the potassium salt is prepared using one equivalent of potassium hydroxide, and the calcium salt, using one equivalent of CaO.

EXAMPLE 12

Preparation of Ethylenediamine Salts of Compounds II

To a solution of 0.50 g of the ammonium salt from Example 10 in 10 ml of methanol is added 0.75 ml of ethylenediamine. The methanol is stripped off under vacuum to obtain the desired ethylenediamine salt.

EXAMPLE 13

Preparation of Tris(hydroxymethyl)aminomethane Salts of Compounds II

To a solution of 202 mg of the ammonium salt from Example 10 in 5 ml of methanol is added a solution of 60.5 mg of tris(hydroxymethyl) aminomethane in 5 ml of methanol. The solvent is removed in vacuo to afford the desired tris(hydroxymethyl)aminomethane salt.

EXAMPLE 14

Preparation of L-Lysine Salts of Compounds II

A solution of 0.001 mole of L-lysine and 0.0011 mole of the ammonium salt from Example 10 in 15 ml of 85% ethanol is concentrated to dryness in vacuo to give the desired L lysine salt.

Similarly prepared are the L-arginine, L-ornithine, and N-methylglucamine salts.

EXAMPLE 15

Preparation of Tetramethylammonium Salts of Compounds II

A mixture of 68 mg of ammonium salt from Example 10 in 2 ml of methylene chloride and 0.08 ml of 24% tetramethylammonium hydroxide in methanol is diluted with ether to yield the desired tetramethylammonium salt.

EXAMPLE 16

Preparation of Methyl Esters of Compounds II

To a solution of 400 mg of lactone from Example 1 in 100 ml of absolute methanol is added 10 ml 0.1M sodium methoxide in absolute methanol. This solution is allowed to stand at room temperature for one hour, then is diluted with water and extracted twice with ethyl acetate. The organic phase is separated, dried ($Na_2SO_4$), filtered and evaporated in vacuo to yield the desired methyl ester.

In like manner, by the use of equivalent amounts of propanol, butanol, isobutanol, t-butanol, amylalcohol, isoamylalcohol, 2-dimethylaminoethanol, benzylalcohol, 2-acetamidoethanol and the like, the corresponding esters are obtained.

EXAMPLE 17

Preparation of Free Dihydroxy Acids

The sodium salt of the compound II from Example 11 is dissolved in 2 ml of ethanol water (1:1; v:v) and added to 10 ml of 1N hydrochloric acid from which the dihydroxy acid is extracted with ethyl acetate. The organic extract is washed once with water, dried ($Na_2SO_4$), and evaporated in vacuo with a bath temperature not exceeding 30° C. The dihydroxy acid derivative slowly reverts to the corresponding, parent lactone on standing, but is stable at a pH above 7.

EXAMPLE 18

As a specific embodiment of a composition of this invention, 20 mg of lactone from Example 1, is formulated with sufficient finely divided lactose to provide a total amount of 580 to 590 mg to fill a size 0, hard-gelatin capsule.

What is claimed is:

1. A compound represented by the following structural formula (I):

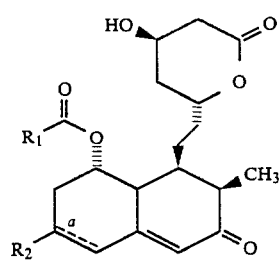

(I)

wherein:
$R_1$ is selected from:
(I) $C_{1-10}$ alkyl;

(2) substituted $C_{1-10}$ alkyl in which one or more substituent(s) is selected from
  (a) halogen,
  (b) hydroxy,
  (c) $C_{1-10}$ alkoxy,
  (d) $C_{1-5}$ alkoxycarbonyl,
  (e) $C_{1-5}$ acyloxy,
  (f) $C_{3-8}$ cycoalkyl,
  (g) phenyl,
  (h) substituted phenyl in which substituents are X and Y,
  (i) $C_{1-10}$ alkylS(O)$_n$ in which n is 0 to 2,
  (j) $C_{3-8}$ cycloalkylS(O)$_n$,
  (k) phenylS(O)$_n$,
  (l) substituted phenylS(O)$_n$ in which the substituents are X and Y, and
  (m) oxo;
(3) $C_{1-10}$ alkoxy;
(4) $C_{2-10}$ alkenyl;
(5) $C_{3-8}$ cycloalkyl;
(6) substituted $C_{3-8}$ cycloalkyl in which one substituent is selected from
  (a) $C_{1-10}$ alkyl
  (b) substituted $C_{1-10}$ alkyl in which the substituent is selected from
    (i) halogen,
    (ii) hydroxy,
    (iii) $C_{1-10}$ alkoxy,
    (iv) $C_{1-5}$ alkoxycarbonyl,
    (v) $C_{1-5}$ acyloxy,
    (vi) phenyl,
    (vii) substituted phenyl in which the substituents are X and Y
    (viii) $C_{1-10}$ alkylS(O)$_n$,
    (ix) $C_{3-8}$ cycloalkylS(O)$_n$,
    (x) phenylS(O)$_n$,
    (xi) substituted phenylS(O)$_n$ in which the substituents are X and Y, and
    (xii) oxo,
  (c) $C_{1-10}$ alkylS(O)$_n$,
  (d) $C_{3-8}$ cycloalkylS(O)$_n$,
  (e) phenylS(O)$_n$,
  (f) substituted phenylS(O)$_n$ in which the substituents are X and Y,
  (g) halogen,
  (h) hydroxy,
  (i) $C_{1-10}$ alkoxy,
  (j) $C_{1-5}$ alkoxycarbonyl,
  (t) $C_{1-5}$ acyloxy,
  (l) phenyl, and
  (m) substituted phenyl in which the substituents are X and Y;
(7) phenyl;
(8) substituted phenyl in which the substituents are X and Y;
(9) amino;
(10) $C_{1-5}$ alkylamino;
(11) di($C_{1-5}$ alkyl)amino;
(12) phenylamino;
(13) substituted phenylamino in which the substituents are X and Y;
(14) phenyl $C_{1-10}$ alkylamino;
(15) substituted phenyl $C_{1-10}$ alkylamino in which the substituents are X and Y;
(16) $R_3S$ in which $R_3$ is selected from
  (a) $C_{1-10}$ alkyl,
  (b) phenyl, and (c) substituted phenyl in which the substituents are X and Y;
R₂ is H, CH₃, or CH₂OH;
X and Y are independently selected from:
  (a) OH,
  (b) halogen,
  (c) trifluoromethyl,
  (d) $C_{1-3}$ alkoxy,
  (e) $C_{1-3}$ alkylcarbonyloxy,
  (f) phenylcarbonyloxy,
  (g) $C_{1-3}$ alkoxycarbonyl,
  (h) phenyloxycarbonyl,
  (i) hydrogen;
  (j) $C_{2-5}$ alkyl;
halogen is Cl or F;
a is a single bond or a double bond.

2. A compound of claim 1 wherein:
R₁ is selected from:
  (1) $C_{1-10}$ alkyl;
  (2) substituted $C_{1-10}$ alkyl in which one or more substituent(s) is selected from
    (a) halogen,
    (b) hydroxy,
    (c) $C_{1-10}$ alkoxy,
    (d) $C_{1-5}$ alkoxycarbonyl,
    (e) $C_{1-5}$ acyloxy,
    (f) $C_{3-8}$ cycloalkyl,
    (g) phenyl,
    (h) substituted phenyl in which the substituents are X and Y, and
    (i) oxo;
  (3) $C_{3-8}$ cycloalkyl;
  (4) substituted $C_{3-8}$ cycloalkyl in which one substituent is selected from
    (a) $C_{1-10}$ alkyl,
    (b) substituted $C_{1-10}$ alkyl in which the substituent is selected from
      (i) halogen,
      (ii) hydroxy,
      (iii) $C_{1-10}$ alkoxy
      (iv) $C_{1-5}$ acyloxy,
      (v) $C_{1-5}$ alkoxycarbonyl,
      (vi) phenyl,
      (vii) substituted phenyl in which the substituents are X and Y, and
      (viii) oxo,
    (c) halogen,
    (d) hydroxy,
    (e) $C_{1-10}$ *alkoxy*,
    (f) $C_{1-5}$ alkoxycarbonyl,
    (g) $C_{1-5}$ acyloxy,
    (h) phenyl,
    (i) substituted phenyl in which the substituents are X and Y;
  (5) phenylamino;
  (6) substituted phenylamino in which the substituents are X and Y;
  (7) phenyl$C_{1-10}$alkylamino; and
  (8) substituted phenyl $C_{1-10}$ alkylamino in which the substituents are X and Y;
X and Y are independently selected from:
  (a) OH,
  (b) F,
  (c) trifluoromethyl,
  (d) $C_{1-3}$ alkoxy,
  (e) hydrogen,
  (f) $C_{1-5}$ alkyl.

3. A compound of claim 2 wherein: R₁ is $C_{1-10}$ alkyl.

4. A compound of claim 3 wherein:
R₁ is 2-butyl or 2-methyl-2-butyl;
R₂ is H or CH₃.

5. A compound of claim 4 selected from the group consisting of:
  (1) 6(R)-[2-[(S)-(2-methylbutyryloxy)-2(S),6-dimethyl-3-oxo-1,2,3,7,8,8a(R)-hexahydronaphthyl-1(S)]ethyl]-4(R)-hydroxy-3,4,5,6-tetrahydro-2H-pyran-2-one;
  (2) 6(R)-[2-[8-(S)-(2,2-dimethylbutyryloxy)-2(S),6-dimethyl-3-oxo-1,2,3,7,8,8a(R)-hexahydronaphthyl-1(S)]ethyl]-4(R)-hydroxy-3,4,5,6-tetrahydro-2H-pyran-2-one;
  (3) 6(R)-[2-[8(S)-(2-methylbutyryloxy)-2(S)-methyl-3-oxo-1,2,3,7,8,8a(R)-hexahydronaphthyl-1(S)]ethyl]-4(R)-hydroxy-3,4,5,6-tetrahydro-2H-pyran-2-one;
  (4) 6(R)-[2-[8(S)-(2,2-dimethylbutyryloxy)-2(S)-methyl-3-oxo-1,2,3,7,8,8a(R)-hexahydronaphthyl-1(S)]ethyl]-4(R)-hydroxy-3,4,5,6-tetrahydro-2H-pyran-2-one;
  (5) 6(R)-[2-[8(S)-(2,2-dimethylbutyryloxy)-2(S),6(R)-dimethyl-3-oxo-1,2,3,5,6,7,8,8a(R)-octahydronaphthyl-1(S)]ethyl]-4(R)-hydroxy-3,4,5,6-tetrahydro-2H-pyran-2-one;
  (6) 6(R)-[2-[8(S)-(2,2-dimethylbutyryloxy)-2(S)-methyl-3-oxo-1,2,3,5,6,7,8,8a(R)-octahydronaphthyl-1(S)]ethyl]-4(R)-hydroxy-3,4,5,6-tetrahydro-2H-pyran-2-one;
  (7) 6(R)-[2-[8(S)-(2-methylbutyryloxy)-2(S),6(R)-dimethyl-3-oxo-1,2,3,5,6,7,8,8a(R)-octahydronaphthyl-1(S)]ethyl]-4(R)-hydroxy-3,4,5,6-tetrahydro-2H-pyran-2-one;
  (8) 6(R)-[2-[8(S)-(2-methylbutyryloxy)-2-(S)-methyl-3-oxo-1,2,3,5,6,7,8,8a(R)-octahydronaphthyl-1(S)]ethyl]-4(R)-hydroxy-3,4,5,6-tetrahydro-2H-pyran-2-one.

6. A hypocholesterolemic, hypolipidemic pharmaceutical composition comprising a nontoxic therapeutically effective amount of a compound of claim 1 and a pharmaceutically acceptable carrier.

7. A composition of claim 6 wherein the therapeutically effective compound is selected from the group consisting of:
  (1) 6(R)-[2-[8(S)-(2-methylbutyryloxy)-2(S),6-dimethyl-3-oxo-1,2,3,7,8,8a(R)-hexahydronaphthyl-1(S)]ethyl]-4(R)-hydroxy-3,4,5,6-tetrahydro-2H-pyran-2-one;
  (2) 6(R)-[2-[8(S)-(2,2-dimethylbutyryloxy)-2(S),6-dimethyl-3-oxo-1,2,3,7,8.8a(R)-hexahydronaphthyl-1(S)]ethyl]-4(R)-hydroxy-3,4,5,6-tetrahydro-2H-pyran-2-one;
  (3) 6(R)-[2-[8(S)-(2-methylbutyryloxy)-2(S)-methyl-3-oxo-1,2,3,7,8,8a(R)-hexahydronaphthyl-1(S)]ethyl]-4(R)-hydroxy-3,4,5,6-tetrahydro-2H-pyran-2-one;
  (4) 6(R)-[2-[8(S)-(2,2-dimethylbutyryloxy)-2(S)-methyl-3-oxo-1,2,3,7,8,8a(R)-hexahydronaphthyl-1(S)]ethyl]-4(R)-hydroxy-3,4,5,6-tetrahydro-2H-pyran-2-one;
  (5) 6(R)-[2-[8(S)-(2,2-dimethylbutyryloxy)-2(S),6(R)-dimethyl-3-oxo-1,2,3,5,6,7,8,8a(R)-octahydronaphthyl-1(S)]ethyl]-4(R)-hydroxy-3,4,5,6-tetrahydro-2H-pyran-2-one;
  (6) 6(R)-[2-[8(S)-(2,2-dimethylbutyryloxy)-2(S)-methyl-3-oxo-1,2,3,5,6,7,8,8a(R)-octahydronaphthyl-1(S)]ethyl]-4(R)-hydroxy-3,4,5,6-tetrahydro-2H-pyran-2-one;

(7) 6(R)-[2-[8(S)-(2-methylbutyryloxy)-2(S),6(R)-dimethyl-3-oxo-1,2,3,5,6,7,8,8a(R)-octahydronaphthyl-1(S)ethyl]-4(R)-hydroxy-3,4,5,6-tetrahydro-2H-pyran-2-one;

(8) 6(R)-[2-[8(S)-(2-methylbutyryloxy)-2(S)-methyl-3-oxo-1,2,3,5,6,7,8,8a(R)-octahydronaphthyl-1(S)ethyl]-4(R)-hydroxy-3,4,5,6-tetrahydro-2H-pyran-2-one.

8. A hypocholesterolimic, hypolipidemic pharmaceutical composition comprising a nontoxic therapeutically effective amount of a compound of claim 1 in combination with a pharmaceutically acceptable nontoxic cationic polymer capable of binding bile acids in a non reabsorbable form in the gastrointestinal tract and a pharmaceutically acceptable carrier.

9. A method of treating hypercholesterolemia comprising the administration to a subject in need of such treatment a nontoxic therapeutically effective amount of a compound of claim 1.

10. A method of claim 9 wherein the therapeutically effective compound is selected from the group consisting of:

(1) 6(R)-[2-[8(S)-(2-methylbutyryloxy)-2(S),6-dimethyl-3-oxo-1,2,3,7,8,8a(R)-hexahydronaphthyl-1(S)ethyl]-4(R)-hydroxy-3,4,5,6-tetrahydro-2H-pyran-2-one;

(2) 6(R)-[2-[8(S)-(2,2-dimethylbutyryloxy)-2(S),6-dimethyl-3-oxo-1,2,3,7,8,8a(R)-hexahydronaphthyl-1(S)ethyl]-4(R)-hydroxy-3,4,5,6-tetrahydro-2H-pyran-2-one;

(3) 6(R)-[2-[8(S)-(2-methylbutyryloxy)-2(S)-methyl-3-oxo-1,2,3,7,8,8a(R)-hexahydronaphthyl-1(S)ethyl]-4(R)-hydroxy-3,4,5,6-tetrahydro-2H-pyran-2-one;

(4) 6(R)-[2-[8(S)-(2,2-dimethylbutyryloxy)-2(S)-methyl-3-oxo-1,2,3,7,8,8a(R)-hexahydronaphthyl-1(S)ethyl]-4(R)-hydroxy-3,4,5,6-tetrahydro-2H-pyran-2-one;

(5) 6(R)-[2-[8(S)-(2,2-dimethylbutyryloxy)-2(S),6(R)-dimethyl-3-oxo-1,2,3,5,6,7,8,8a(R)-octahydronaphthyl-1(S)ethyl]-4(R)-hydroxy-3,4,5,6-tetrahydro-2H-pyran-2-one;

(6) 6(R)-[2-[8(S)-(2,2-dimethylbutyryloxy)-2(S)-methyl-3-oxo-1,2,3,5,6,7,8,8a(R)-octahydronaphthyl-1(S)ethyl]-4(R)-hydroxy-3,4,5,6-tetrahydro-2H-pyran-2-one;

(7) 6(R)-[2-[8(S)-(2-methylbutyryloxy)-2(S),6(R)-dimethyl-3-oxo-1,2,3,5,6,7,8,8a(R)-octahydronaphthyl-1(S)ethyl]-4(R)-hydroxy-3,4,5,6-tetrahydro-2H-pyran-2-one;

(8) 6(R)-[2-[8(S)-(2-methylbutyryloxy)-2(S)-methyl-3-oxo-1,2,3,5,6,7,8,8a(R)-octahydronaphthyl-1(S)ethyl]-4(R)-hydroxy-3,4,5,6-tetrahydro-2H-pyran-2-one.

* * * * *